United States Patent [19]

Holt et al.

[11] Patent Number: 5,041,433

[45] Date of Patent: Aug. 20, 1991

[54] 11-KETO OR HYDROXY 3,5-DIENE STEROIDS AS INHIBITORS OF STERIOD 5-α-REDUCTASE

[75] Inventors: Dennis A. Holt, Mohnton; Brian W. Metcalf, Radnor; Mark A. Levy, Wayne, all of Pa.

[73] Assignee: SmithKline Beecham Corporation, Philadelphia, Pa.

[21] Appl. No.: 430,152

[22] Filed: Nov. 1, 1989

Related U.S. Application Data

[63] Continuation-in-part of Ser. No. 182,828, Apr. 18, 1988, abandoned, which is a continuation-in-part of Ser. No. 127,147, Dec. 1, 1987, Pat. No. 4,910,226, which is a continuation-in-part of Ser. No. 43,773, Apr. 29, 1987, abandoned.

[51] Int. Cl.$^5$ .................... A61K 31/58; A61K 31/56; C07J 43/00; C07J 41/00; C07J 13/00; C07J 1/00; C07J 31/00

[52] U.S. Cl. .................... 514/176; 514/177; 514/179; 514/182; 540/108; 540/110; 552/531; 552/532; 552/544; 552/552; 552/555; 552/603; 552/611; 552/643

[58] Field of Search ............ 552/531, 532, 544, 552, 552/555, 603, 611, 634; 514/176, 177, 179, 182; 540/108, 110

[56] References Cited

U.S. PATENT DOCUMENTS

| | | |
|---|---|---|
| 4,191,759 | 3/1980 | Johnston et al. ............... 260/397.1 |
| 4,317,817 | 3/1982 | Blohm et al. ..................... 260/349 |
| 4,361,578 | 11/1982 | Alig et al. ......................... 549/331 |
| 4,377,584 | 3/1983 | Rasmusson et al. ............. 546/77 |
| 4,814,324 | 3/1989 | Borris et al. ..................... 536/5 |
| 4,910,226 | 3/1990 | Holt et al. ........................ 514/573 |

FOREIGN PATENT DOCUMENTS

0289327  11/1988  European Pat. Off. .

OTHER PUBLICATIONS

Hsia and Voight, J. Invest. Dermat. 62:224–227 (1974).
Robaire et al., J. Steroid Biochem. 8:307–310 (1977).
Blohm, T. R., et al., Biochem. Biophys. Res. Comm. 95:273–280 (1980).
Liang, T., et al., J. Steroid Biochm. 19:385–390 (1983).
Petrow, V., et al., Steroids 38:121–140 (1981).
Brookds et al., Steroids: 47:1–19 (Jan. 1986).

*Primary Examiner*—Frederick E. Waddell
*Assistant Examiner*—Kimberly Jordan
*Attorney, Agent, or Firm*—Wayne J. Dustman; Stuart R. Suter; Edward T. Lentz

[57] ABSTRACT

Invented are carboxyl and carboxyl alkyl ester substituted 11-keto and hydroxy analogues of synthetic steroidal compounds, pharmaceutical compositions containing these compounds, and methods of using these compounds to inhibit steroid 5-α-reductase.

28 Claims, No Drawings

11-KETO OR HYDROXY 3,5-DIENE STEROIDS AS INHIBITORS OF STERIOD 5-α-REDUCTASE

This is a continuation-in-part of U.S. application Ser. No. 182,828, filed Apr. 18, 1988, now abandoned, which is a continuation-in-part of U.S. application Ser. No. 127,147, filed Dec. 1, 1987, now U.S. Pat. No. 4,910,226, which is a continuation-in-part of U.S. application Ser. No. 043,773, filed Apr. 29, 1987, now abandoned.

FIELD OF THE INVENTION

The present invention relates to certain novel carboxyl and carboxyl ester substituted 11-keto and hydroxy analogues of synthetic steroidal compounds, pharmaceutical compositions containing these compounds, and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testis. Steroid 5-α-reductase is an NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley et al., *J. Steroid Biochem.* 11: 637–648 (1979).

Recognition of the importance of elevated DHT levels in many disease states has stimulated many efforts to synthesize inhibitors of this enzyme. The structures of several known steroid 5-α-reductase inhibitors are shown in Table 1.

TABLE 1

| | 5-α-Reductase Inhibitors | | |
|---|---|---|---|
| | | $K_i$ | Reference |
| (1) | 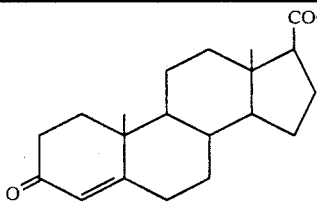 | $1.1 \times 10^{-6}$ M (Reversible) | Hsia and Voight, 1973 |
| (2) | 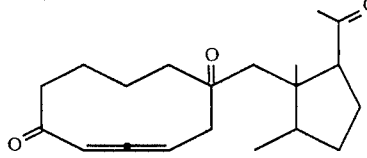 | $1 \times 10^{-6}$ M (Irreversible) | Robaire et al., 1977 |
| (3) | 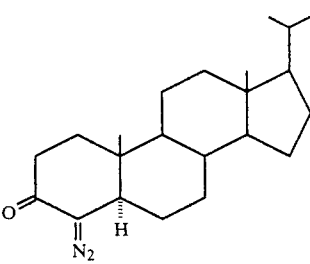 | $3.5 \times 10^{-8}$ (Irreversible) | Blohm et al., 1980 |
| (4) | 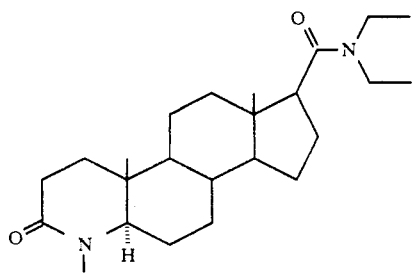 | $5 \times 10^{-9}$ M (Reversible) | Liang et al., 1983 |

TABLE 1-continued

| | 5-α-Reductase Inhibitors | |
|---|---|---|
| | $K_i$ | Reference |
| (5) | $1.25 \times 10^{-6}$ M (Irreversible) | Petrow et al., 1981 |

The first inhibitor described was the 17-β-carboxylic acid (1) by Hsia and Voight in 1973. *J. Invest. Dermat.* 62: 224–227. The secosteroid (2) was the next inhibitor to be described and also has found utility as an affinity label for 5-α-reductase. Robaire et al., *J. Steroid Biochem.* 8: 307–310 (1977). The diazoketone (3) has been reported as a potent, time-dependent inhibitor of steroid 5-α-reductase. Blohm et al., *Biochem. Biophys. Res. Comm.* 95: 273–280 (1980); U.S. Pat. No. 4,317,817, issued Mar. 2, 1982. Compound (4) is exemplary of a group of 4-aza steroid inhibitors of steroid 5-α-reductase described in U.S. Pat. No. 4,377,584, issued Mar. 22, 1983, and in Liang et al., *J. Steroid Biochem.* 19: 385–390 (1983). The 6-methylene steroid (5) also has been shown to be a time-dependent inactivator of steroid 5-α-reductase. Petrow et al., *Steroids* 38: 121–140 (1981).

Other steroid 5-α-reductase inhibitors also have been described. U.S. Pat. No. 4,361,578, issued June 2, 1986, describes a class of homosteroid enzyme inhibitors. U.S. Pat. No. 4,191,759, issued Mar. 4, 1980, discloses amides of 17β-carboxy-4-androsten-3-one that are active as steroid 5-α-reductase inhibitors. Japanese Patents J60146855-A and J60116657-A disclose various aniline derivatives having numerous activities including 5-α-reductase including activity. Japanese Patent J60142941-A discloses phenyl-substituted ketones having 5-α-reductase inhibiting activity, and European Patent EP173516-A discloses various phenyl-substituted amides having similar activity. Shiseido referenced terpene derivatives that are active inhibitors of steroid 5-α-reductase. Japanese Patent No. J59053417-A.

Palladium-catalyzed carbonylation of substituted androstene derivatives has been described. Cacchi et al., *Tet. Letters* 26: 1109–1112 (1985). No biological activity for the synthesized compounds, however, is disclosed.

Preparation of steroidal 3-chloro-3,5-dienes has been described in Deghenghi et al., *Canadian J. Chem.* 40: 818–820 (1962).

Use of phosphorous trihalides to convert steroidal Δ⁴-3-ketones to corresponding 3-halo-3,5-dienes has been reported Ross et al., *J. Org. Chem.* 29: 2784–2785 (1964).

SUMMARY OF THE INVENTION

The present invention resides in the discovery that steroid 5-α-reductase is inhibited by certain carboxyl and carboxyl alkyl ester substituted 11-keto or hydroxy 3,5-diene analogues of synthetic steroidal compounds. The compounds are potent enzyme inhibitors.

Presently preferred compounds of the invention and compounds used in the invented pharmaceutical compositions and the invented methods include methyl 17β-(N,N-diisopropylcarboxamide)-11-oxo-androsta-3,5-diene-3-carboxylate;

ethyl 17β-(N,N-diisopropylcarboxamide)-11-oxo-androsta-3,5-diene-3-carboxylate;

17β-(N,N-diisopropylcarboxamide)-11-oxo-androsta-3,5-diene-3-carboxylic acid;

17β-(N,N-diisopropylcarboxamide)-11β-hydroxy-androsta-3,5-diene-3-carboxylic acid;

methyl 17β-(N-t-butylcarboxamide)-11-oxo-androsta-3,5-diene-3-carboxylate;

ethyl 17β-(N-t-butylcarboxamide)-11-oxo-androsta-3,5-diene-3-carboxylate;

17β-(N-t-butylcarboxamide)-11-oxo-androsta-3,5-diene-3-carboxylic acid; and

17β-(N-t-butylcarboxamide)-11β-hydroxy-androsta-3,5-diene-3-carboxylic acid.

In a further aspect of the invention there are provided novel intermediates formed during the process of preparing the presently invented 5-α-reductase inhibiting compounds.

The invention also provides a method for inhibiting 5-α-reductase activity in mammals, including humans, that comprises administering internally to a subject in need thereof an effective amount of a presently invented 5-α-reductase inhibiting compound.

Included in the present invention are pharmaceutical compositions comprising a pharmaceutical carrier and compounds useful in the methods of the invention.

DETAILED DESCRIPTION OF THE INVENTION

The presently invented compounds that inhibit 5-α-reductase have the following Formula (I):

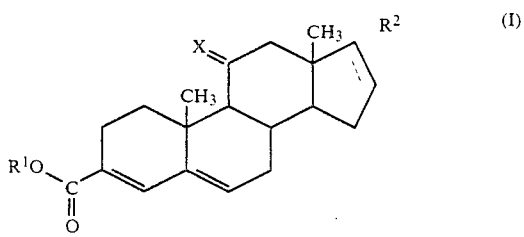

in which:

the D ring has an optional double bond where indicated by the broken line, provided that the D ring does not have a $C_{16}$-$C_{17}$ double bond when $R^2$ represents two substituents or a divalent substituent;

X is
(1) keto, or
(2) a hydrogen atom and a hydroxyl group;

$R^1$ is H or $C_{1-8}$alkyl; and $R^2$ is
(1) α-hydrogen, α-hydroxyl, or α-acetoxy and/or

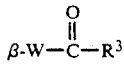

where W is a bond or $C_{1-12}$alkyl, and $R^3$ is
(i) $C_{1-8}$alkyl,
(ii) $C_{1-8}$alkoxy, or
(iii) $N(R^4)_2$, where each $R^4$ is independently selected from hydrogen, $C_{1-8}$alkyl, $C_{3-6}$cycloalkyl, phenyl; or both $R^4$ taken together with the nitrogen to which they are attached represent a 5-6 membered saturated ring comprising up to one other heteroatom selected from oxygen and nitrogen;
(2) =CH—W—CO—$R^3$ or =CH—W—$OR^5$, where W and $R^3$ have the same meaning as above, and $R^5$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) $C_{1-8}$alkyl, or
(vii) $C_{1-20}$alkylcarbonyl;
(3) α-hydrogen and β-$NHCOR^6$ where $R^6$ is $C_{1-12}$alkyl or β-$N(R^4)_2$ where $R^4$ has the same meaning as above, or
(4) keto;
or a pharmaceutically acceptable salt thereof.

As used herein, unless otherwise specified, $C_{1-n}$alkyl and $C_{1-n}$alk mean a straight or branched hydrocarbon chain having 1 to n carbons and Alk means a straight or branched hydrocarbon chain having 1 to 12 carbons.

Preferred among the presently invented compounds are those having, as the $R^2$ substituent, α-hydrogen and β-$CON(R^4)_2$. Particularly preferred of such compounds are those where each $R^4$ is independently selected from hydrogen and $C_{1-8}$alkyl.

Compounds of the Formula (I), or pharmaceutically acceptable salts thereof, are included in the pharmaceutical compositions of the invention, and used in the methods of the invention.

As used above and throughout the remainder of the specification and claims, the carbons of the steroid nucleus are numbered and the rings are lettered as follows:

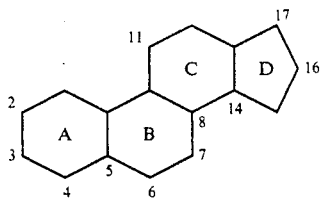

The following Scheme I may be used to prepare the compounds of Formula (I) of the instant invention.

The formula (a) starting compounds of Scheme I may be prepared by oxidation of known precursors, such as corticosterone or derivatives thereof. For example, corticosterone, dissolved in an organic solvent such as methanol, may be contacted with an aqueous solution of periodic acid to yield androst-4-ene-3-one-11-ol-17β-carboxylic acid. A starting compound of formula (a) may then be obtained by treating the androst-4-ene-3-one-11-ol-17β-carboxylic acid, dissolved in an organic solvent such as acetone, with Jones reagent to yield androst-4-ene-3,11-dione-17β-carboxylic acid. European Patent Publication No. 0,289,327, published Nov. 2, 1988 (European Patent Application No. 88303878.8), incorporated herein by reference.

Alternatively, corticosterone, in an appropriate solvent such as acetone, may be treated directly with Jones reagent to yield androst-4-ene-3,11-dione-17β-carboxylic acid.

In Scheme I, $R^7$ is $R^2$ or moieties which can be chemically converted to those of $R^2$ by known chemical reactions, such as those described in J. Fried and J. Edwards, *Organic Reactions in Steroid Chemistry*, Pub: Van Nostrand Reinhold Company (1972), provided that $R^7$ does not include any such moieties that render inoperative the Scheme I process. For example, compounds wherein $R^7$ is carboxylic acid may be converted to the corresponding amides by reaction with amines or substituted amines, via the corresponding acid chlorides. Reactions to convert $R^7$ to $R^2$ may be performed on products of the synthetic pathways of Scheme I or, where appropriate or preferable, on certain intermediates in those synthetic pathways.

SCHEME I

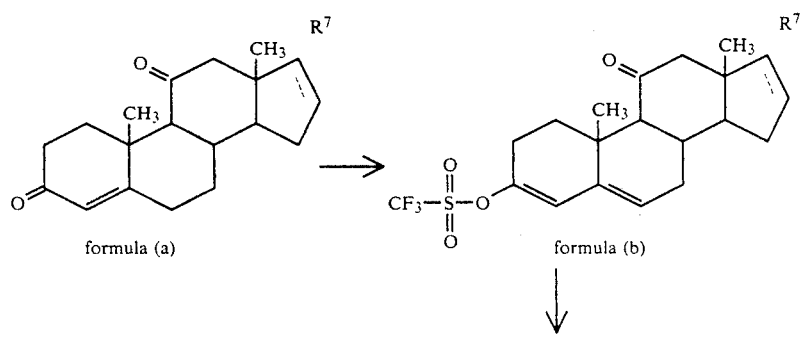

SCHEME I

-continued

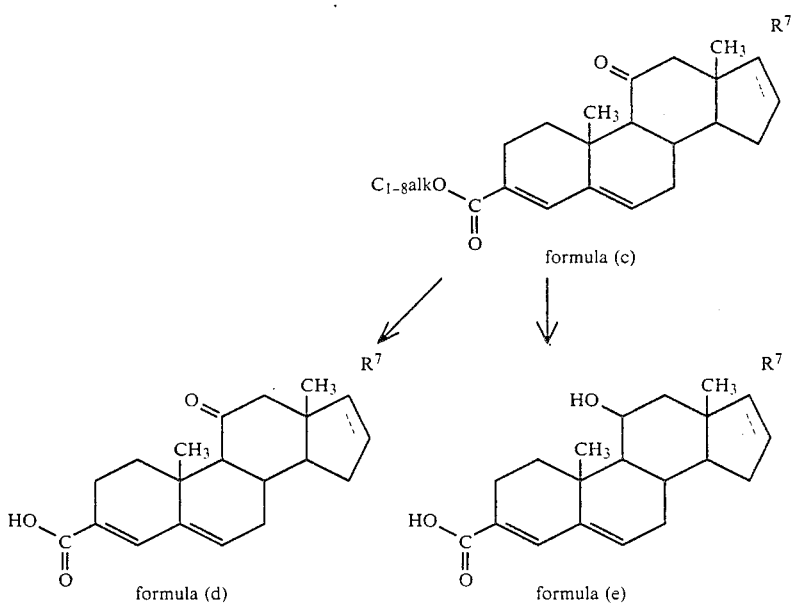

formula (c)

formula (d)     formula (e)

According to Scheme I, to a formula (a) compound dissolved in an appropriate organic solvent, preferably methylene chloride, is added 2,6-di-t-butyl-4-methylpyridine. A trihaloalkyl sulfonic anhydride, preferably trifluoromethane sulfonic anhydride, is then added to yield a compound of formula (b).

To the formula (b) compound dissolved in a suitable organic solvent such as dimethylformamide (DMF) are added an organic base such as trimethylamine, or, preferably, triethylamine, a palladium (II) compound such as palladium (II) acetate, a phosphine compound such as triphenylphosphine, and a $C_{1-8}$alkanol, followed by addition of CO to give a compound of formula (c).

A compound of the formula (d) may be prepared, if desired, by hydrolysis of the compound of formula (c), for example, by contact with an alkaline agent such as potassium carbonate.

Alternatively, a compound of the formula (e) may be prepared, if desired, by both hydrolysis and reduction of the compound of formula (c), the latter with a reducing agent such as sodium borohydride.

In preparing the compounds of Formula (I) of the present invention, novel intermediates of the following Formula (II) are synthesized:

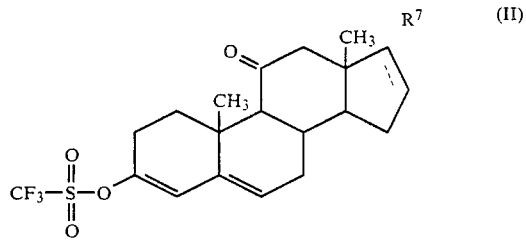

(II)

in which $R^7$ is defined as above.

Pharmaceutically acceptable base addition salts of compounds of Formula (I) of the invention containing an acidic group may be prepared by known methods from organic and inorganic bases, which may include nontoxic alkali metal and alkaline earth bases such as calcium, sodium, and potassium hydroxide; ammonium hydroxide, and nontoxic organic bases such as triethylamine, butylamine, piperazine, and (trihydroxymethyl)methylamine.

Because Formula (I) compounds, or pharmaceutically acceptable salts thereof, inhibit steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy and prostatic cancer, and male pattern baldness. As inhibitors of steroid-5-α-reductase, Formula (I) compounds, or pharmaceutically acceptable salts thereof, also improve urodynamics. That is, these compounds or salts relieve problems with urination, even prior to shrinkage of prostate size.

Compounds of the invention were tested for potency in inhibiting human steroid 5-α-reductase using tissue from hyperplastic human prostates. In determining potency in inhibiting the human enzyme, the following procedure was employed:

Frozen human prostates were thawed and minced into small pieces (5 mm$^3$). The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier (Branson Sonic Power Co.) followed by hand homogenization in a glass-to-glass Dounce homogenizer (Kontes Glass Company, Vineland, N.J.).

Prostatic particles were obtained by differential centrifugation at 600 or 1000×g for 20 minutes and 140,000×g for 60 minutes at 4° C. The pellet obtained from the 140,000×g centrifugation was washed with 5 to 10 tissue volumes of the buffer described above and recentrifuged at 140,000×g. The resulting pellet was suspended in 20 mM potassium phosphate buffer, pH 6.5, containing 20% glycerol, 1 mM dithiothreitol, 50 μM NADPH. The suspended particulate solution was stored at −80° C.

A constant amount of [$^{14}$C]-testosterone (52 to 55 mCi/mmol, New England Nuclear, Boston, Mass.) in ethanol and varying amounts of the potential inhibitor in ethanol were deposited in test tubes and concentrated to dryness in a SAVANT Speed Vac. To each tube was added buffer, 20 μl of 10 mM NADPH and an aliquot of prostatic particulate solution to a final volume of 0.5 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androstandediol, and androstanedione as carriers. The organic layer was removed to a second test tube and evaporated to dryness in a Speed Vac. The residue was dissolved in 20 to 30 μl chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from Equation 1:

$$K_i = (B/A)/(S/K_m + 1) \qquad \text{Equation 1}$$

where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 μM.

Table 2 displays the results of the above testing, and shows that the tested compounds of the invention are potent inhibitors of human steroid 5-α-reductase.

TABLE 2

| Inhibition Constants of Human Prostatic Steroid 5-α-Reductase | | |
|---|---|---|
| Compound | | $K_i$(nM) |
| (1) | 17β-(N,N-diisopropylcarboxamide)-11-oxo-androsta-3,5-diene-3-carboxylic acid | 30 |
| (2) | 17β-(N,N-diisopropylcarboxamide)-11β-hydroxy-androsta-3,5-diene-3-carboxylic acid | 20 |

Additionally, suppression of DHT concentration has been observed in vivo, upon use of a compound of Formula (I) in a primate screen.

The compounds of Formula (I), or pharmaceutically acceptable salts thereof, may be incorporated into convenient dosage forms such as capsules, tablets, or injectable preparations. Solid or liquid pharmaceutical carriers or diluents may be employed. Exemplary solid carriers include starch, lactose, calcium sulfate dihydrate, terra alba, sucrose, talc, gelatin, agar, pectin, acacia, magnesium stearate, and stearic acid. Exemplary liquid carriers include syrup, peanut oil, olive oil, saline, and water. The carrier or diluent may include any prolonged release material, such as glyceryl monostearate or glyceryl distearate, alone or with a wax. The amount of solid carrier may vary widely but, preferably, will be from about 25 mg to about 1 g per dosage unit. When a liquid carrier is used, the preparation may be in the form of a syrup, elixir, emulsion, soft gelatin capsule, sterile injectable liquid such as an ampoule, or an aqueous or nonaqueous liquid suspension.

The pharmaceutical preparations may be made following conventional techniques of the pharmaceutical chemist, involving mixing, granulating, and compressing, as appropriate, for tablet forms, or mixing, filling and dissolving the ingredients, as appropriate, to give the desired oral or parenteral products.

Doses of the present compounds of Formula (I), or pharmaceutically acceptable salts thereof, in a pharmaceutical dosage unit as described above will be an efficacious, nontoxic quantity selected from the range of 0.1–1000 mg/kg of active compound, preferably 1–100 mg/kg. The selected dose may be administered to a human patient in need of steroid 5-α-reductase inhibition from 1–6 times daily, topically, orally, rectally, by injection, or continuously by infusion. Oral dosage units for human administration preferably contain from 1 to 500 mg of active compound.

The present invention also includes methods of inhibiting steroid 5-α-reductase activity in mammals, including humans, comprising administering a compound of Formula (I), or a pharmaceutically acceptable salt thereof, internally to a subject in need of such inhibition in an effective steroid 5-α-reductase inhibiting amount. The invented methods of reducing prostate size, which include methods of reducing the rate at which prostate size increases or maintaining prostate size, comprise administering internally to a subject an effective amount of a Formula (I) compound, or pharmaceutically acceptable salt thereof.

Contemplated equivalents of Formula (I) compounds are compounds, for example, otherwise corresponding thereto wherein substituents have been added to any of the unsubstituted positions of the Formula (I) compounds, or, for example, the methyl groups at $C_{10}$ or $C_{13}$ are absent or replaced by $C_{2-4}$alkyl, provided such compounds have equivalent pharmaceutical utility to Formula (I) compounds.

The following examples illustrate preparation of compounds of the invention and pharmaceutical compositions containing these compounds. The examples are not intended to limit the scope of the invention as defined hereinabove and as claimed below.

EXAMPLE 1

Methyl 17β-(N,N-Diisopropylcarboxamide)-11-oxo-androsta-3,5-diene-3-carboxylate (i) 3,11-Oxo-4-androsten-17β-carboxylic Acid To a solution of corticosterone (4.0 g, 11.5 mmol) in acetone (150 ml) cooled to 0° C. was added 20 ml of Jones reagent (prepared according to *Org. Syn. Coll.*, Vol. V, p. 866). After 1.5 hours an additional 2 ml of Jones reagent was added and the mixture was allowed to stir for an additional 30 minutes. The volatiles were removed in vacuo and the residue was diluted with water and extracted with ethyl acetate. The organic extract was washed with water and brine, then dried and evaporated. Trituration with methanol provided 2.1 g (55%) of the title compound.

(ii)
3,11-Oxo-4-androsten-17β-(N,N-diisopropyl-carboxamide)

To an azeotropically dried suspension of 3,11-oxo-4-androsten-17β-carboxylic acid (4.7 g, 14 mmol) in 450 ml toluene at 0° C. was added pyridine (1.7 ml, 20 mmol), followed by oxalyl chloride (2.0 ml, 23 mmol) in 25 ml toluene. The mixture was allowed to warm to room temperature, and was stirred for 2 hours. Excess oxalyl chloride was removed by distillation at reduced pressure of 100 ml of the toluene. The resulting mixture was cooled to 0° C. and diisopropylamine (25 ml, 180 mmol) was added slowly. After stirring overnight the volatiles were removed in vacuo. The residue was dissolved in dichloromethane and washed with water, dilute HCl, and brine, and then dried and concentrated. The crude product was chromatographed (silica gel, 3:1-hexane: ethyl acetate) to yield 3.2 g (56%) of the title compound as a white solid, m.p. 213°–215° C.

(iii)
11-Oxo-3-(trifluoromethanesulfonate)-3,5-androstadien-17β-(N,N-diisopropylcarboxamide)

To a solution of 3,11-oxo-4-androsten-17β-(N,N-diisopropylcarboxamide) (3.28 g, 8 mmol) and 2,6-di-t-butyl-4-methylpyridine (2.05 g, 10 mmol) in 150 ml dichloromethane was added trifluoromethane sulfonic anhydride (1.8 ml, 10.7 mmol). After 2.5 hours the volatiles were removed in vacuo. Chromatography of the residue (silica gel, 1:4-ethyl acetate: hexane) yielded 3.15 g (72%) of the title compound as a white crystalline solid, m.p. 157°–159° C.

(iv) Methyl 17β-(N,N-Diisopropylcarboxamide)-11-oxo-androsta-3,5-diene-3-carboxylate A mixture of 11-oxo-3-(trifluoromethanesulfonate)-3,5-androsta-dien-17β-(N,N-diisopropylcarboxamide) (3.1 g), palladium (II)acetate (0.15 g), triphenylphosphine (0.35 g), triethylamine (15.6 ml), methanol (20 ml), and dimethylformamide (20 ml) was heated at 60° C. under one atmosphere of carbon monoxide for 2.5 hours. After cooling, the mixture was diluted with water and thoroughly extracted with ethyl acetate. The organic extract was washed with water, dilute HCl, and brine, and then dried and concentrated. The residue was chromatographed (silica gel, 3:7-ethyl acetate: hexanes) to yield 1.45 g (56%) of the title compound as a white solid, m.p.=156° C.

EXAMPLE 2

17β-(N,N-Diisopropylcarboxamide)-11-oxo-androsta-3,5-diene-3-carboxylic Acid

A mixture of methyl 17β-(N,N-diisopropylcarboxamide)-11-oxo-androsta-3,5-diene-3-carboxylate (150 mg) and K₂CO₃ (200 mg) in 10 ml ethanol and 1 ml water was heated at reflux for 4 hours. The mixture was cooled, acidified with dilute HCl, and extracted with ethyl acetate. The organic extract was concentrated and the residue was recrystallized from acetone to yield the title compound as a white solid, m.p.=250°–252° C.

EXAMPLE 3

17β-(N,N-Diisopropylcarboxamide)-11β-hydroxyandrosta-3,5-diene-3-carboxylic Acid To a solution of methyl 17β-(N,N-diisopropylcarboxamide)-11-oxo-androsta-3,5-diene-3-carboxylate (100 mg) in tetrahydrofuran (10 ml) was added 5% aqueous NaOH (2 ml) and NaBH₄ (200 mg). The mixture was heated and refluxed overnight, and then cooled, diluted with water and extracted with ethyl acetate. The extract was washed with water and brine, and then dried and concentrated. Chromatography (silica gel, 1:3-ethyl acetate: hexanes, 1% acetic acid) of the residue followed by recrystallization from acetone afforded the title compound, m.p.=180° C.

EXAMPLE 4

Methyl 17β-(N-t-Butylcarboxamide)-11-oxo-androsta-3,5-diene-3-carboxylate

The title compound is prepared according to Example 1, steps (i) through (iv), wherein tert-butylamine is substituted for diisopropylamine in step (ii) of Example 1.

EXAMPLE 5

17β-(N-t-Butylcarboxamide)-11-oxo-androsta-3,5-diene-3-carboxylic Acid

The title compound is prepared according to Example 2 wherein methyl 17β-(N-t-butylcarboxamide)-11-oxo-androsta3,5-diene-3-carboxylate is substituted for methyl 17β-(N,N-diisopropylcarboxamide)-11-oxo-androsta-3,5-diene-3-carboxylate.

EXAMPLE 6

17β-(N-t-Butylcarboxamide)-11β-hydroxy-androsta-3,5-diene-3-carboxylic Acid

The title compound is prepared according to Example 3 wherein methyl 17β-(N-t-butylcarboxamide)-11-oxo-androsta-3,5-diene-3-carboxylate is substituted for methyl 17β-(N,N-diisopropylcarboxamide)-11-oxo-androsta-3,5-diene-3-carboxylate.

EXAMPLE 7

Ethyl 17β-(N,N-Diisopropylcarboxamide)-11-oxo-androsta-3,5-diene-3-carboxylate

The title compound is prepared according to Example 1, steps (i) through (iv), wherein ethanol is substituted for methanol in step (iv) of Example 1.

EXAMPLE 8

Ethyl 17β-(N-t-Butylcarboxamide)-11-oxo-androsta-3,5-diene-3-carboxylate

The title compound is prepared according to Example 1, steps (i) through (iv), wherein tert-butylamine is substituted for diisopropylamine in step (ii) of Example 1 and wherein ethanol is substituted for methanol in step (iv) of Example 1.

EXAMPLE 9

An oral dosage form for administering Formula (I) compounds is produced by screening, mixing, and filling into hard gelatin capsules the ingredients in the proportions shown in Table 3, below.

TABLE 3

| Ingredients | Amounts |
| --- | --- |
| 17β-(N,N-diisopropylcarboxamide)-11-oxo-androsta-3,5-diene-3-carboxylic acid | 50 mg |

TABLE 3-continued

| Ingredients | Amounts |
| --- | --- |
| magnesium stearate | 5 mg |
| lactose | 75 mg |

EXAMPLE 10

The sucrose, calcium sulfate dihydrate and Formula (I) compound shown in Table 4 below, are mixed and granulated in the proportions shown with a 10% gelatin solution. The wet granules are screened, dried, mixed with the starch, talc and stearic acid, screened and compressed into a tablet.

TABLE 4

| Ingredients | Amounts |
| --- | --- |
| 17β-(N-t-butylcarboxamide)-11-oxo-androsta-3,5-diene-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 11

17β-(N,N-Diisopropylcarboxamide)-11β-hydroxyandrosta-3,5-diene-3-carboxylic acid (1.0 g) is dissolved in 20 g of soybean oil and emulsified by mixing with 1.2 g of egg phospholipid and enough water to bring the final volume to 100 ml. The formed interlipid formulation is suitable for intravenous administration.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the Formula (I)

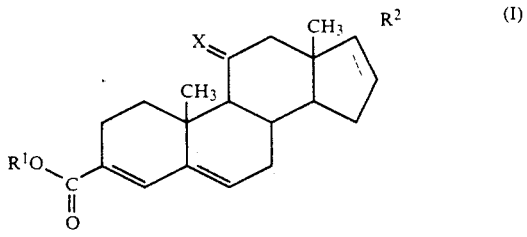

in which:
the D ring has an optional double bond where indicated by the broken line, provided that the D ring does not have a $C_{16}$-$C_{17}$ double bond when $R^2$ represents two substituents or a divalent substituent;

X is
(2) keto, or
(2) a hydrogen atom and a hydroxyl group;

$R^1$ is H or $C_{1-8}$alkyl; and $R^2$ is
(1) α-hydrogen, α-hydroxyl, or α-acetoxy and/or

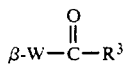

where W is a bond or $C_{1-12}$alkyl, and $R^3$ is (i) $C_{1-8}$alkyl,
(ii) $C_{1-8}$alkoxy, or
(iii) $N(R^4)_2$, where each $R^4$ is independently selected from hydrogen, $C_{1-8}$alkyl, $C_{3-6}$cycloalkyl, phenyl; or both $R^4$ taken together with the nitrogen to which they are attached represent a 5–6 membered saturated ring comprising up to one other heteroatom selected from oxygen and nitrogen;

(2) =CH—W—CO—$R^3$ or =CH—W—O$R^5$, where W and $R^3$ have the same meaning as above, and $R^5$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) $C_{1-8}$alkyl, or
(vii) $C_{1-20}$alkylcarbonyl;

(3) α-hydrogen and β-NHCOR$^6$ where $R^6$ is $C_{1-12}$alkyl or β-N(R$^4$)$_2$ where $R^4$ has the same meaning as above, or (4) keto;

or a pharmaceutically acceptable salt thereof.

2. A compound of claim 1, wherein X is keto.

3. A compound of claim 2, wherein $R^1$ is a hydrogen atom.

4. A compound of claim 3, wherein $R^2$ is α-hydrogen and β-CON(R$^4$)$_2$, where each $R^4$ is independently selected from hydrogen and $C_{1-8}$alkyl.

5. A compound of claim 4 selected from the group consisting of:
17β-(N,N-diisopropylcarboxamide)-11-oxo-androsta-3,5-diene-3-carboxylic acid; and
17β-(N-t-butylcarboxamide)-11-oxo-androsta-3,5-diene-3-carboxylic acid.

6. A compound of claim 2, wherein $R^1$ is $C_{1-8}$alkyl.

7. A compound of claim 6, wherein $R^2$ is α-hydrogen and β-CON(R$^4$)$_2$, where each $R^4$ is independently selected from hydrogen and $C_{1-8}$alkyl.

8. A compound of claim 7 selected from the group consisting of:
methyl 17β-(N,N-diisopropylcarboxamide)-11-oxo-androsta-3,5-diene-3-carboxylate;
ethyl 17β-(N,N-diisopropylcarboxamide)-11-oxo-androsta-3,5-diene-3-carboxylate;
methyl 17β-(N-t-butylcarboxamide)-11-oxo-androsta-3,5-diene-3-carboxylate; and
ethyl 17β-(N-t-butylcarboxamide)-11-oxo-androsta-3,5-diene-3-carboxylate.

9. A compound of claim 1, wherein X is a hydrogen atom and a hydroxyl group.

10. A compound of claim 9, wherein $R^1$ is a hydrogen atom.

11. A compound of claim 10, wherein $R^2$ is α-hydrogen and β-CON(R$^4$)$_2$, where each $R^4$ is independently selected from hydrogen and $C_{1-8}$alkyl.

12. A compound of claim 11 selected from the group consisting of:
17β-(N,N-diisopropylcarboxamide)-11α-hydroxyandrosta-3,5-diene-3-carboxylic acid; and
17β-(N-t-butylcarboxamide)-11α-hydroxy-androsta-3,5-diene-3-carboxylic acid.

13. A compound of claim 9, wherein $R^1$ is $C_{1-8}$alkyl.

14. A compound of claim 13, wherein $R^2$ is α-hydrogen and β-CON(R$^4$)$_2$, where each $R^4$ is independently selected from hydrogen and $C_{1-8}$alkyl.

15. A pharmaceutical composition comprising a suitable pharmaceutical carrier, and a compound of claim 1 in which $R^1$ is H.

16. A composition of claim 15, wherein X is keto.

17. A composition of claim 15, wherein X is a hydrogen atom and a hydroxyl group.

18. A composition of claim 15, wherein said compound of claim 1 is selected from the group consisting of:

17β-(N,N-diisopropylcarboxamide)-11-oxo-androsta-3,5-diene-3-carboxylic acid;

17β-(N,N-diisopropylcarboxamide)-11α-hydroxy-androsta-3,5-diene-3-carboxylic acid;

17β-(N-t-butylcarboxamide)-11-oxo-androsta-3,5-diene-3-carboxylic acid; and

17β-(N-t-butylcarboxamide)-11α-hydroxy-androsta-3,5-diene-3-carboxylic acid.

19. A method of inhibiting steroid 5-α-reductase activity in a subject that comprises administering to said subject an effective therefor amount of a compound of claim 1 in which $R^1$ is H.

20. A method of claim 19, wherein X is keto.

21. A method of claim 19, wherein X is a hydrogen atom and a hydroxyl group.

22. A method of claim 19, wherein said compound of claim 1 is selected from the group consisting of:

methyl 17β-(N,N-diisopropylcarboxamide)-11-oxo-androsta-3,5-diene-3-carboxylate;

ethyl 17β-(N,N-diisopropylcarboxamide)-11-oxo-androsta-3,5-diene-3-carboxylate;

17β-(N,N-diisopropylcarboxamide)-11-oxo-androsta-3,5-diene-3-carboxylic acid;

17β-(N,N-diisopropylcarboxamide)-11β-hydroxy-androsta-3,5-diene-3-carboxylic acid;

methyl 17β-(N-t-butylcarboxamide)-11-oxo-androsta-3,5- diene-3-carboxylate;

ethyl 17β-(N-t-butylcarboxamide)-11-oxo-androsta-3,5-diene-3-carboxylate;

17β-(N-t-butylcarboxamide)-11-oxo-androsta-3,5-diene-3-carboxylic acid; and

17β-(N-t-butylcarboxamide)-11-hydroxy-androsta-3,5-diene-3-carboxylic acid.

23. A method of reducing or maintaining prostate size in a subject that comprises administering to said subject an effective therefor amount of a compound of claim 1 in which $R^1$ is H.

24. A method of treating baldness in a subject that comprises administering to said subject an effective therefor amount of a compound of claim 1 in which $R^1$ is H.

25. A method of treating acne in a subject that comprises administering to said subject an effective therefor amount of a compound of claim 1 in which $R^1$ is H.

26. A method of treating hirsutism in a subject that comprises administering to said subject an effective therefor amount of a compound of claim 1 in which $R^1$ is H.

27. A method of improving urodynamics in a subject that comprises administering to said subject an effective therefor amount of a compound of claim 1 in which $R^2$ is H.

28. A compound of the Formula (II)

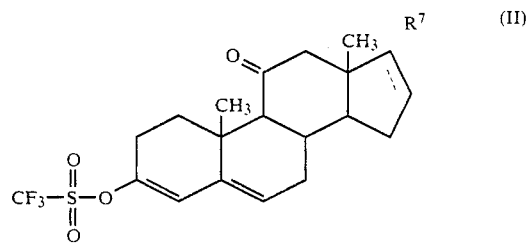

in which:

the D ring has an optional double bond where indicated by the broken line, provided that the D ring does not have a $C_{16}$-$C_{17}$ double bond when $R^7$ represents two substituents or a divalent substituent;

$R^7$ is (1) α-hydrogen, α-hydroxyl, or α-acetoxy and/or

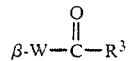

where W is a bond or $C_{1-12}$alkyl, and $R^3$ is (i) $C_{1-8}$alkyl, (ii) $C_{1-8}$alkoxy, or (iii) $N(R^4)_2$, where each $R^4$ is independently selected from hydrogen, $C_{1-8}$alkyl, $C_{3-6}$cycloalkyl, phenyl; or both $R^4$ taken together with the nitrogen to which they are attached represent a 5–6 membered saturated ring comprising up to one other heteroatom selected from oxygen and nitrogen;

(2) =CH—W—CO—$R^3$ or =CH—W—O$R^5$, where W and $R^3$ have the same meaning as above, and $R^5$ is (i) phenyl$C_{1-6}$alkylcarbonyl, (ii) $C_{5-10}$cycloalkylcarbonyl, (iii) benzoyl, (iv) $C_{1-8}$alkoxycarbonyl, (v) aminocarbonyl, or $C_{1-8}$alkyl substituted aminocarbonyl, (vi) $C_{1-8}$alkyl, or (vii) $C_{1-20}$alkylcarbonyl;

(3) α-hydrogen and β-NHCO$R^6$ where $R^6$ is $C_{1-12}$alkyl or β-N($R^4$)$_2$ where $R^4$ has the same meaning as above;

(4) keto; or (5) moieties which can be chemically converted to moieties (1) through (4) above.

* * * * *

UNITED STATES PATENT AND TRADEMARK OFFICE
CERTIFICATE OF CORRECTION

PATENT NO. : 5,041,433
DATED : August 20, 1991
INVENTOR(S) : Holt, Levy, Metcalf It is certified that error appears in the above-indentified patent and that said Letters Patent is hereby corrected as shown below:

In claim 1, column 13, replace
"
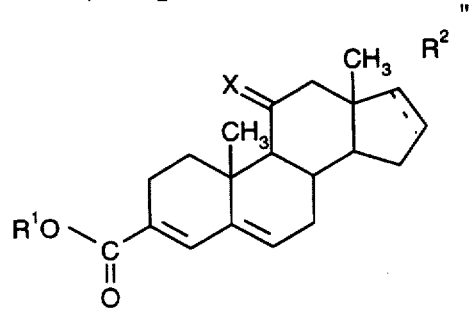
"
with---

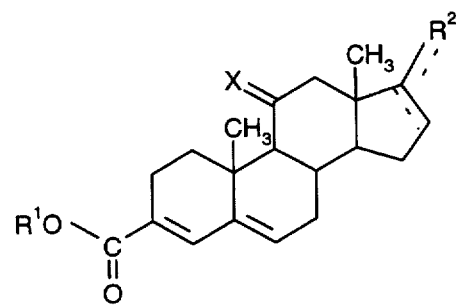
---

In claim 12, column 14, line 61, replace "-11α-hydroxyan-" with -- -11β-hydroxyan- --.

In claim 12, column 14, line 63, replace "-11α-hydroxy-androsta- " with -- -11β-hydroxy-androsta- --.

In claim 18, column 15, line 13, replace "-11α-hydroxy- " with -- -11β-hydroxy- --.

UNITED STATES PATENT AND TRADEMARK OFFICE
CERTIFICATE OF CORRECTION

PATENT NO. : 5,041,433
DATED : August 20, 1991
INVENTOR(S) : Holt, Levy, Metcalf It is certified that error appears in the above-indentified patent and that said Letters Patent is hereby corrected as shown below:

In claim 18, column 15, line 17, replace "-11α-hydroxy-androsta- " with -- -11β-hydroxy-androsta- --.

In claim 22, column 15, lines 29-32, delete "methyl 17β-(N,N-diisopropylcarboxamide)-11-oxo-androsta-3,5-diene-3-carboxylate;
ethyl 17β-(N,N-diisopropylcarboxamide)-11-oxo-androsta-3,5-diene-3-carboxylate;".

In claim 22, column 15, lines 38-41, delete "methyl 17β-(N-t-butylcarboxamide)-11-oxo-androsta-3,5-diene-3-carboxylate;
ethyl 17β-(N-t-butylcarboxamide)-11-oxo-androsta-3,5-diene-3-carboxylate;".

In claim 28, column 16, replace "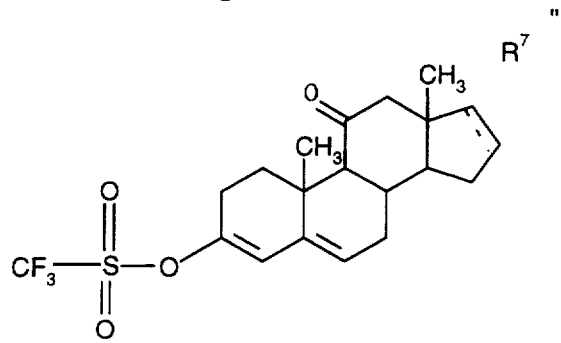"

with

UNITED STATES PATENT AND TRADEMARK OFFICE
CERTIFICATE OF CORRECTION

PATENT NO. : 5,041,433
DATED : August 20, 1991
INVENTOR(S) : Holt, Levy, Metcalf It is certified that error appears in the above-indentified patent and that said Letters Patent is hereby corrected as shown below:

---

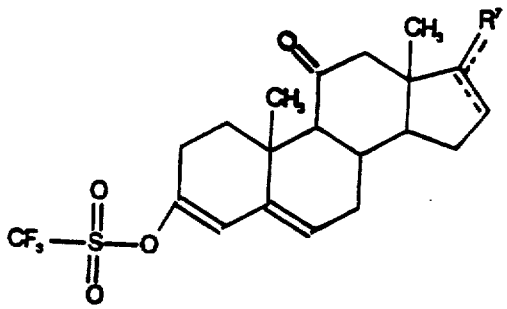

---

Signed and Sealed this

Nineteenth Day of November, 1996

Attest:

BRUCE LEHMAN

Attesting Officer    Commissioner of Patents and Trademarks